US008641599B2

(12) United States Patent
Liao

(10) Patent No.: US 8,641,599 B2
(45) Date of Patent: Feb. 4, 2014

(54) SEXUAL AID DEVICE

(76) Inventor: Ci Sheng Liao, Sinjhuang (TW)

( * ) Notice: Subject to any disclaimer, the term of this patent is extended or adjusted under 35 U.S.C. 154(b) by 701 days.

(21) Appl. No.: 12/888,392

(22) Filed: Sep. 22, 2010

(65) Prior Publication Data

US 2011/0071343 A1 Mar. 24, 2011

(30) Foreign Application Priority Data

Sep. 22, 2009 (TW) ............................ 098217417 U

(51) Int. Cl.
*A61F 5/00* (2006.01)

(52) U.S. Cl.
USPC ........................................................ 600/38

(58) Field of Classification Search
USPC ................ 600/38–41; 623/24, 25, 27, 57, 63, 623/66.1; 128/842, 844, 845; 340/545.5
See application file for complete search history.

(56) References Cited

U.S. PATENT DOCUMENTS 5,229,756 A * 7/1993 Kosugi et al. ................ 345/156
8,353,887 B2 * 1/2013 Matsuura ...................... 604/347
2004/0082831 A1 * 4/2004 Kobashikawa et al. ......... 600/38
2006/0079732 A1 * 4/2006 Blumenthal .................... 600/38
2010/0069706 A1 * 3/2010 Rousere ......................... 600/33

FOREIGN PATENT DOCUMENTS

JP 3172168 * 11/2011

* cited by examiner

*Primary Examiner* — Samuel Gilbert

(57) ABSTRACT

A sexual aid device includes a sheath body and a sensor module. The sheath body has first and second sheath bodies capable of being assembled and separated mutually, and the first and the second sheath bodies construct a containing space. The sensor module is disposed on the first sheath body, and includes a printed circuit board, a controlling switch, a vibration switch and an outputting port. The controlling switch performs sensing and controls the vibration switch to be started. The vibration switch outputs vibration signals for controlling the output port to transmit the vibration signal out. An interactive media is used in cooperation so as to raise the practicability and sensory organ stimulation.

10 Claims, 6 Drawing Sheets

SEXUAL AID DEVICE

BACKGROUND OF THE INVENTION

1. Field of the Invention

The present invention relates to a technique to raise personal sexual pleasure, and more particularly, to a sexual aid device for a man's genitals.

2. Description of the Related Art

Because of human body structure, a person has various desires, from birth through adulthood, and these desires include food desires, shopping desires, money desires, sexual desire and so on. In terms of sexual desire, if one has a stable relationship with another person, he/she can relieve his/her sexual desire and achieve effects of physical and mental health. If one is single, the best way to fulfill sexual desire is through various sex toys, which is not only sanitary and convenient, but also results in less complicated sexual issues.

Because sex toys can fulfill sexual desire and are convenient for storage, more and more sexual toys of various structures are on the market. Not only can a single person fulfill sexual desire with sex toys, but also people with a partner can raise their sexual pleasure and sexual life and then make their relationship harmonious by the sexual toys. In medical science, it has been proven that men have a greater sexual desire than women due to their human body structure, and therefore there are a wide variety of sex toys available for male masturbation.

A conventional sexual device for men is like what is disclosed in Taiwan Pat. No. M358641. The patent discloses a counting sleeve ring with counting function. The counting sleeve ring has a counting device inside to count the moving times of a man's genitals and a wireless signal module for sending wireless signals. The module generates different signals according to each value of times counted by the counting device of the sleeve ring. A CPU decides to trigger and start corresponding sensory organ stimulating module according to signals received, so as to achieve the objective of raising sexual pleasure.

However, a preset vibration time needs to be set before using such sexual device, so that the sensory organ stimulating module is started after a user vibrates for a certain times. Therefore, the user can predict when the sensory organ stimulating module is started, and there is no new and stimulating feeling after usage for a while. Besides, the sensory organ stimulating module only has vibration and sound effect and does not have visual stimulating effects, resulting in decrease of overall practicability.

SUMMARY OF THE INVENTION

The main objective of the present invention is to provide a sexual aid device, cooperating with an interactive media for use, so as to raise overall practicability and sensory organ stimulation.

Another objective of the present invention is to provide a sexual aid device, cooperating with a man's masturbating sheath, so as to raise overall comfort and safety.

Still another objective of the present invention is to provide a sexual aid device with simple overall structure, so as to lower manufacture and production cost.

To achieve the above-mentioned objectives, the present invention discloses a sexual aid device including a sheath body and a sensor module. The sheath body has first and second sheath bodies capable of being assembled and separated mutually, and the first and the second sheath bodies construct a containing space. The sensor module is disposed on the first sheath body, and includes a printed circuit board (PCB), a controlling switch electrically connected to the PCB, a vibration switch disposed on the PCB and an outputting port. The controlling switch performs sensing and controls the vibration switch to be started. The vibration switch outputs vibration signals for controlling the output port to transmit the vibration signal out.

In a preferred embodiment, the sheath body is a cylindrical sheath body, and a man's masturbating sheath is disposed in the containing space. The output port is also electrically connected with an interactive media of a computer.

Compared to conventional techniques, a man's masturbating sheath can be disposed in the containing space of the sexual aid device in the present invention. A man's genitals can be directly disposed in the masturbating sheath to start the controlling switch and achieves the objective of controlling the vibration switch to transmit the vibration signals, and then the vibration signals are transmitted to an externally connected computer through the output port, and interaction with interactive media of the computer is created, so that the user has sensory organ stimulation of various aspects including touching, hearing and vision simultaneously, so as to raise the overall practicability and sensory organ stimulation.

Figure 1:
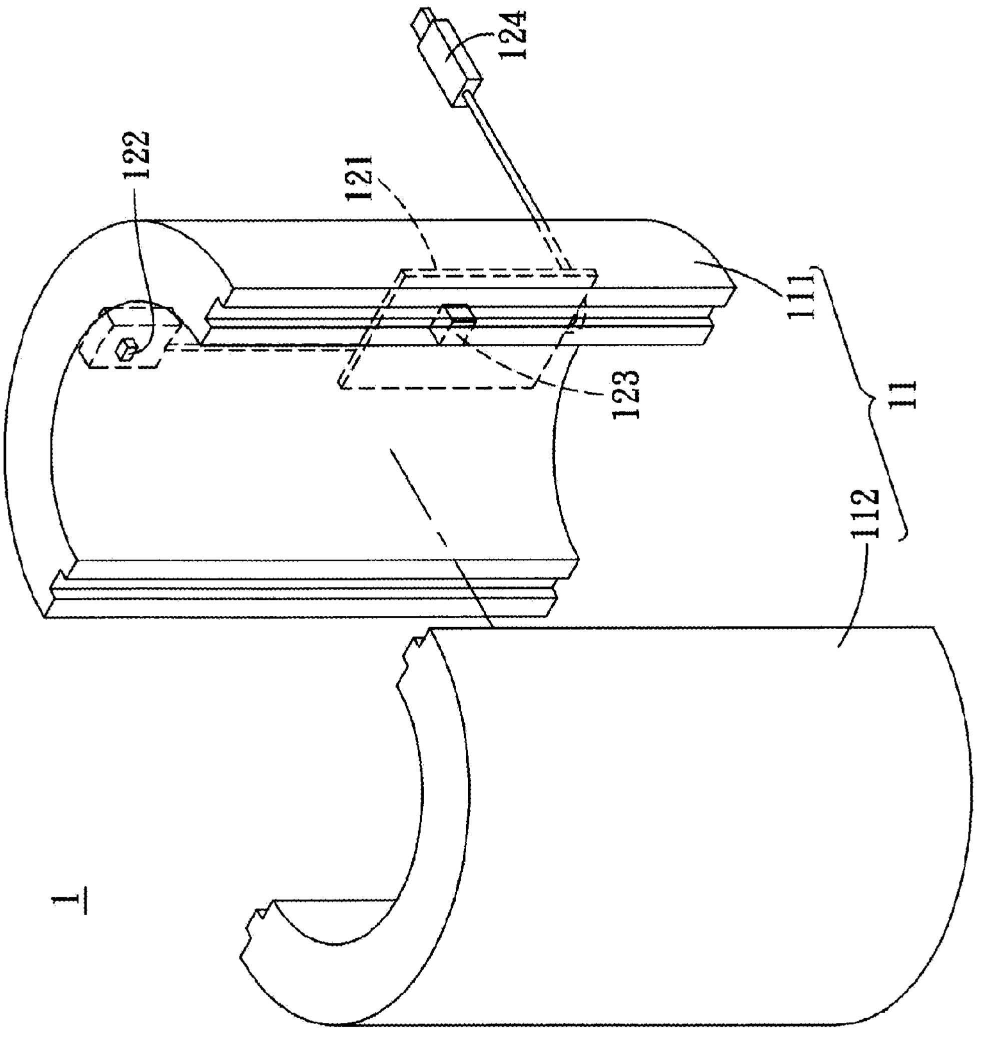
FIG. 1 is an exploded perspective view showing a sexual aid device in a preferred embodiment of the present invention.

NUMERICAL SYMBOLS (1) sexual aid device
(11) sheath body
(110) containing space
(111) first sheath body
(112) second sheath body
(12) sensor module
(121) Printed Circuit Board (PCB)
(122) controlling switch
(123) vibration switch
(124) output port
(2) man's masturbating sheath
(21) through hole
(3) man's genitals
(4) notebook

DETAILED DESCRIPTION OF THE PREFERRED EMBODIMENT

Specific preferred embodiments below describe the practice method of the present invention, and people skilled in the art can easily understand other advantages and effects of the present invention from the content disclosed by the specification.

The preferred embodiments of the present invention are described referring to the figures. It should be noted that the figures below are simplified schematic drawings and describe the basic idea of the present invention in a schematic way. That is, the figures illustrate structures related to the present invention and are not drawn according to the number, shape and size of components in practical embodiments. It is clarified that the shape, number and ratio of each component in practical embodiments are not limited to what is shown in the figures and can be changed according to actual design requirements.

Figure 2:
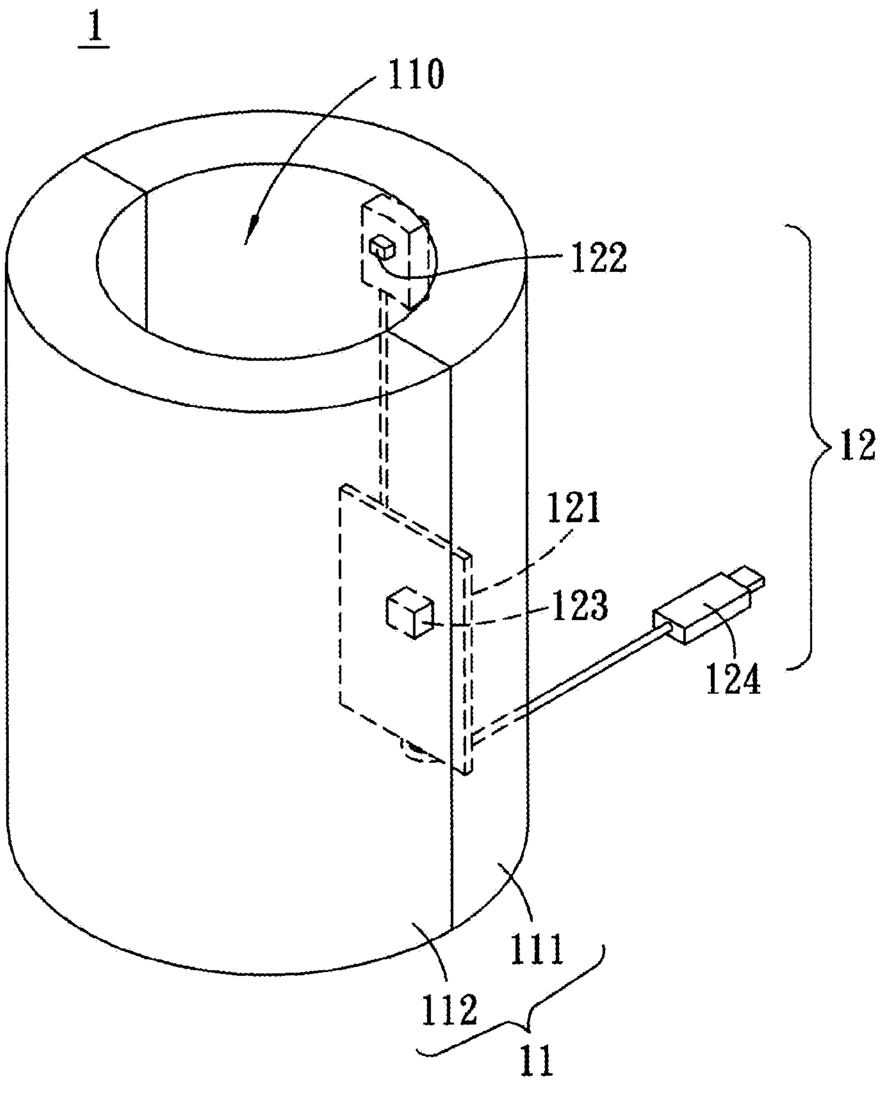
FIG. 2 is an assembled perspective view showing a sexual aid device in a preferred embodiment of the present invention.
Figure 3:
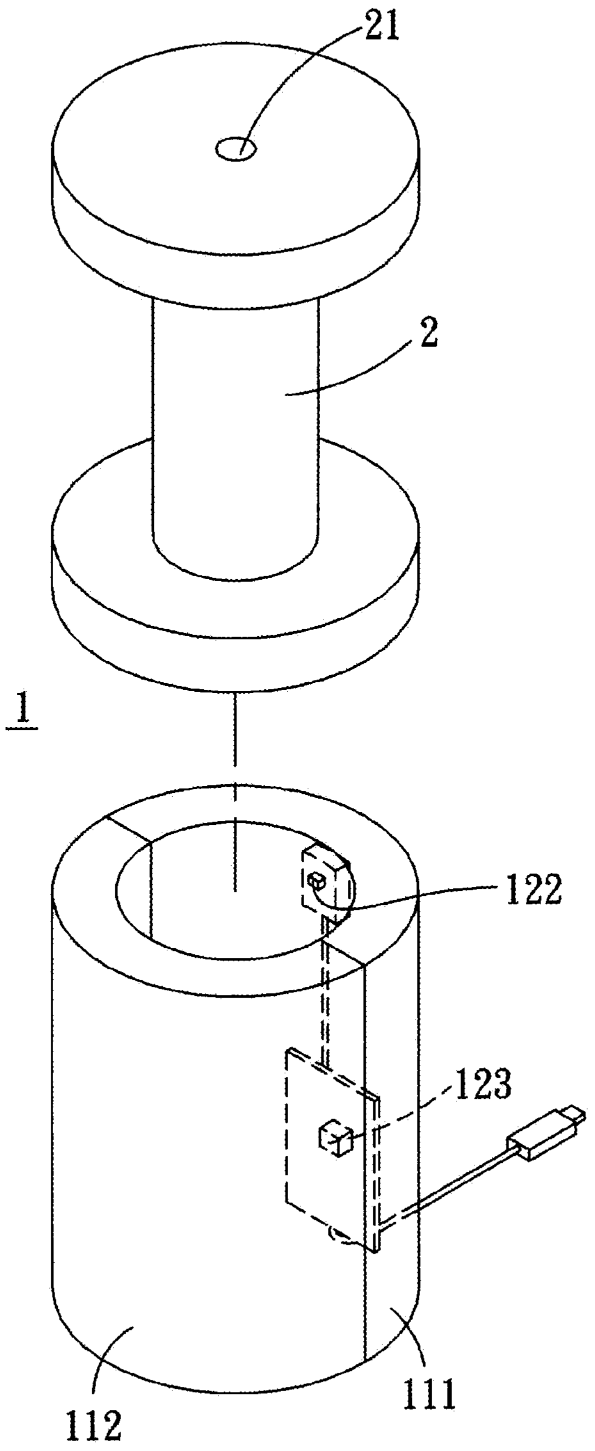
FIG. 3 is an exploded perspective view showing a sexual aid device in another preferred embodiment of the present invention.

First, please refer to FIG. 1 and FIG. 2, which are the exploded and the assembled perspective views of a sexual aid device in a preferred embodiment of the present invention. As shown in the figure, a sexual aid device 1 of the present invention includes a sheath body 11 and a sensor module 12.

The sheath body 11 has first and second sheath bodies 111 and 112 capable of being assembled and separated mutually, and the first and the second sheath bodies 111 and 112 construct a containing space 110.

A sensor module 12 is disposed on the first sheath body 111, and includes a printed circuit board (hereinafter, "PCB") 121, a controlling switch 122, a vibration switch 123 and an output port 124. The controlling switch 122 is electrically connected to the PCB 121. The vibration switch 123 is disposed on the PCB 121 and is electrically connected to the PCB 121. One end of the output port 124 is electrically connected to the PCB 121 and the other end protrudes out of the first sheath body 111 which can be electrically connected to an external computer or notebook (not shown in the figure). The first sheath body 111 has a top end and a bottom end. The controlling switch 122 is near the top end and the PCB 121 is near the bottom end. Besides, the controlling switch 122 performs sensing and controls the vibration switch 123 to be started. The vibration switch 123 outputs vibration signals which are transmitted out to the external computer or notebook through the output port 124.

In the preferred embodiment, the sheath body 11 is a cylindrical sheath body 11, and the first sheath body 111 and the second sheath body 122 are both semi-cylindrical, but they are not limited accordingly. In other preferred embodiments, the sheath body 11 can also be of other shapes with similar effects. The controlling switch 122 can be a mechanical controlling switch 122, a light-sensing controlling switch 122 or a touch-sensing controlling switch 122. The vibration switch 123 can be a ball switch, a mercury switch, a swing switch or a switch with equivalent effect.

Figure 4:
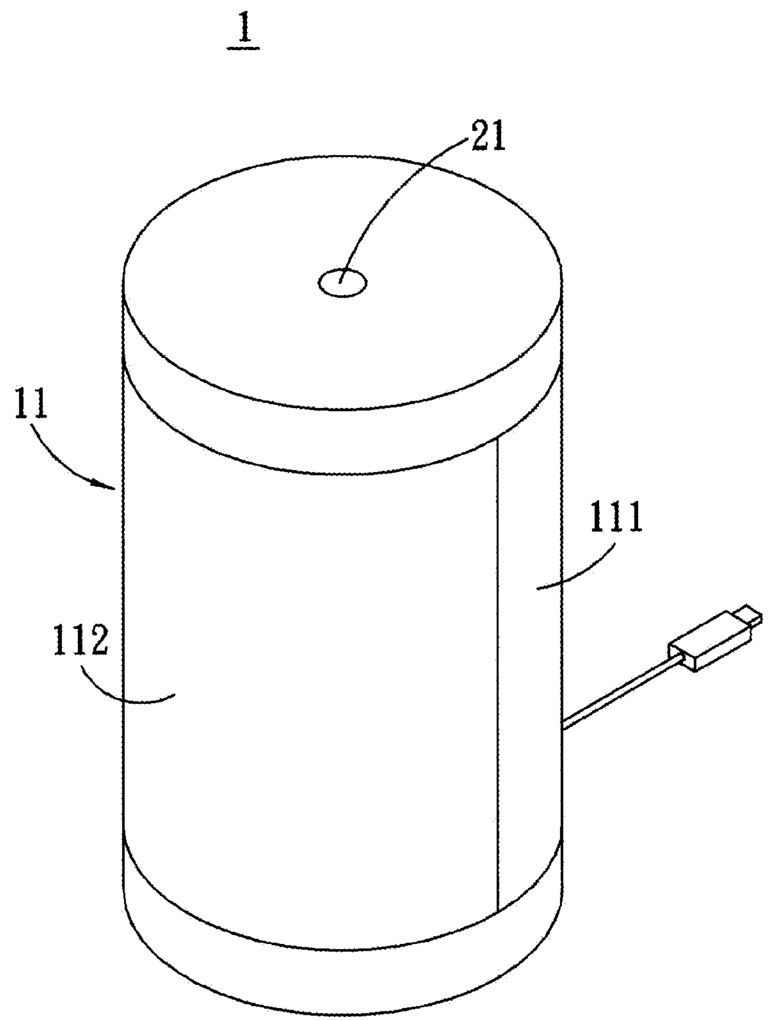
FIG. 4 is an assembled perspective view showing a sexual aid device in another preferred embodiment of the present invention.
Figure 5:
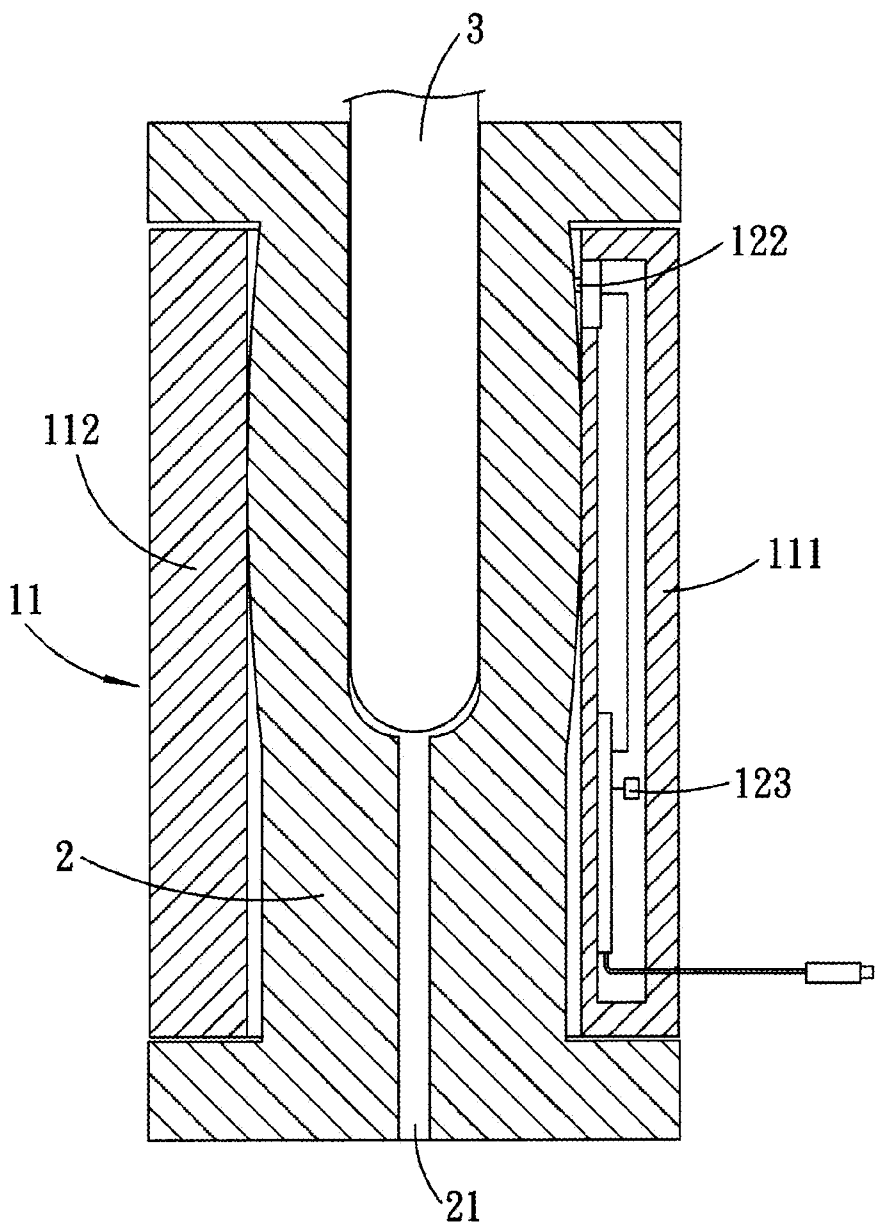
FIG. 5 is a lateral cross-section view showing a usage situation of asexual aid device in another preferred embodiment of the present invention.
Figure 6:
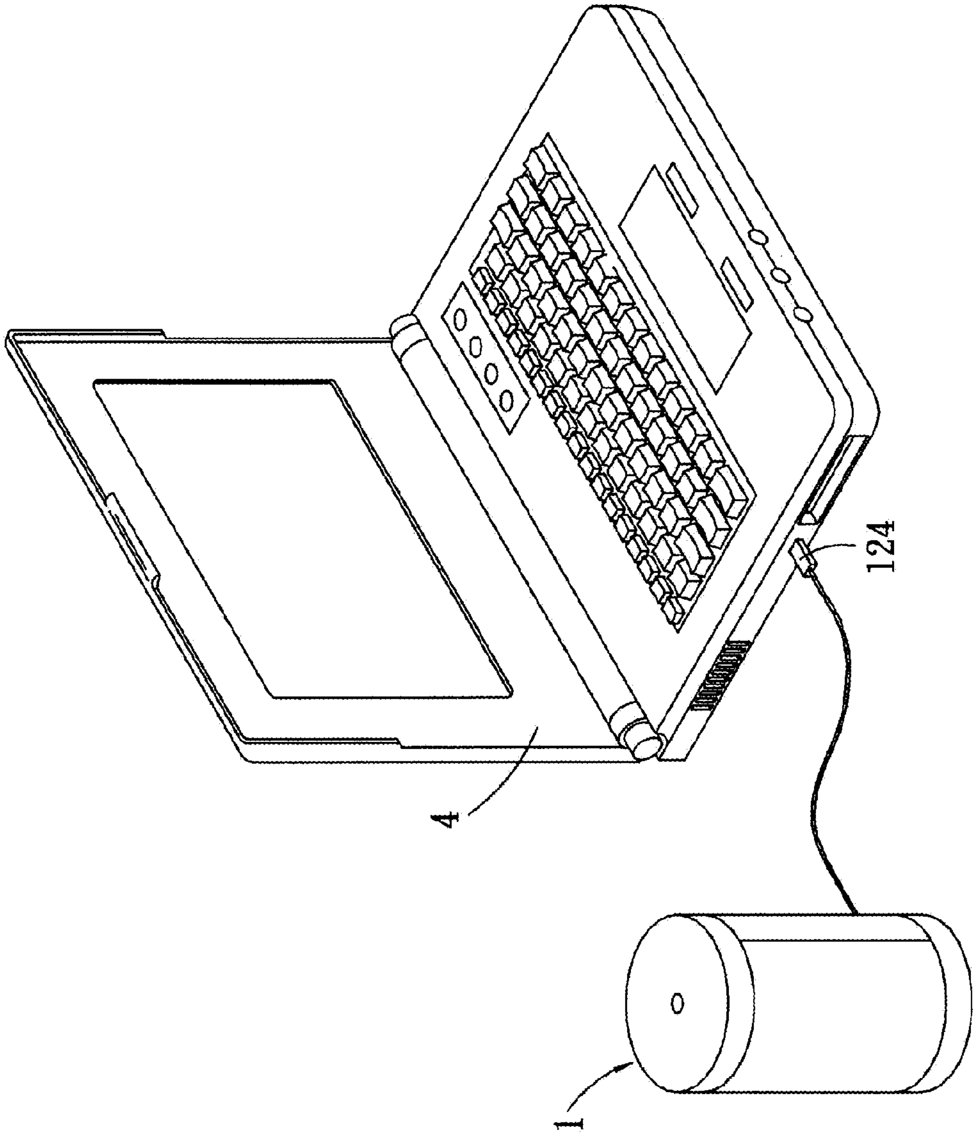
FIG. 6 is a reference view showing another usage situation of a sexual aid device of the present invention.

Please refer to FIG. 3, FIG. 4, FIG. 5 and FIG. 6, which are an exploded perspective view and an assembled perspective view of a sexual aid device of the present invention, and a lateral cross-section view of a usage situation and a reference view showing another usage situation of a sexual aid device of the present invention. As shown in the figures, a sexual aid device 1 is mainly used cooperating with a man's masturbating sheath 2. A first sheath body 111 and a second sheath body 122 wrap the man's masturbating sheath 2 to locate the man's masturbating sheath 2 in a containing space 110. The top end and the bottom end of the man's masturbating sheath 2 protrude out of the sexual aid device 1 (as shown in FIG. 4). In the preferred embodiment, the man's masturbating sheath 2 is a man's masturbating sheath of silicon rubber, and thus has better elasticity. A through hole 21 is disposed in the middle of the man's masturbating sheath 2. In practical usage, a man's genitals 3 is inserted into the through hole 21, and the man's masturbating sheath 2 expands outwardly by being pressed by the man's genitals 3. The exterior of the man's masturbating sheath 2 presses the controlling switch 122 to make the controlling switch 122 drive the vibration switch 123 to be started. Meanwhile, a user only needs to move the sheath body 11 upwardly and downwardly (which is a man's masturbating behavior), the vibration switch 123 senses vibration of external forces and then sends signals. As shown in FIG. 6, the output port 124 is electrically connected to a computer or a notebook 4. Therefore, after the vibration signals outputted by the vibration switch 123 are coded, they are transmitted to the notebook 4 through the output port 124. Then, a link with the interactive media (such as an interactive video or cartoon) on the notebook 4 is done, and the interaction with the interactive media is performed so as to achieve various sensory organ stimulation including sensing, vision and hearing, and then the optimal usage pleasure is achieved.

Compared to conventional techniques, the sexual aid device of the present invention has a simple overall structure and can be used cooperating with a man's masturbating sheath, raising the practicability of the man's masturbating sheath. Moreover, the interactive media of the computer can be linked to achieve sensory organ stimulation of various aspects, thus there are more simulative and practicability.

Although the preferred embodiments are disclosed in the above-mentioned description and figures, it should be understood that various additions, more modification and substitution can be applied in the preferred embodiments of the present invention, without departing from the spirit and scope of the principle of the invention defined in the accompanying claims. People skilled in the art should realize that many modifications of shape, structure, placement, ratio, material, component and assembly can be applied to the present invention. Thus, the preferred embodiments disclosed in the description should be regarded as description of the present invention and not to limit the present invention. The scope of the present invention should be defined by the accompanying claims and covers similarities by law, and is not limited to the description above.

What is claimed is:

1. A sexual aid device, comprising:

a sheath body defining a containing space, the sheath body having first and second sheath bodies removably assembled with each other and each defining a portion of the containing space, and when assembled the first and the second sheath bodies form the containing space; and a sensor module, being disposed on or in the first sheath body and including a printed circuit board (PCB), a controlling switch electrically connected to the PCB, a vibration switch disposed on the PCB, and an outputting port, the controlling switch controlling operations of the vibration switch, the vibration switch sensing vibrations and outputting corresponding vibration signals for controlling the output port to transmit the vibration signals out to another device.

2. The sexual aid of claim 1, wherein the sheath body is a cylindrical sheath body.

3. The sexual aid device as claimed in claim 1, wherein a man's masturbating sheath is disposed in the containing space.

4. The sexual aid device as claimed in claim 3, wherein the man's masturbating sheath is made from silicon rubber.

5. The sexual aid device as claimed in claim 1, wherein the controlling switch is a mechanical controlling switch.

6. The sexual aid device as claimed in claim 1, wherein the controlling switch is a light-sensing controlling switch.

7. The sexual aid device as claimed in claim 1, wherein the vibration switch is a ball switch, a mercury switch or a swing switch.

8. The sexual aid device as claimed in claim 1, wherein the output port is adapted to electrically connect to a computer.

9. The sexual aid device as claimed in claim 8, wherein the computer comprises an interactive media and the interactive media is an interactive video or an interactive cartoon responsive to the vibration signals.

10. The sexual aid device as claimed in claim 1, wherein the first sheath body has a top end and a bottom end, the controlling switch being near the top end and the PCB being near the bottom end.

* * * * *